(12) United States Patent
Solem et al.

(10) Patent No.: US 11,123,468 B2
(45) Date of Patent: Sep. 21, 2021

(54) FILTERING OF PRESSURE SIGNALS FOR SUPPRESSION OF PERIODIC PULSES

(71) Applicant: Gambro Lundia AB, Lund (SE)

(72) Inventors: Kristian Solem, Kavlinge (SE); Bo Olde, Lund (SE); Jan Sternby, Lund (SE)

(73) Assignee: Gambro Lundia AB, Lund (SE)

( * ) Notice: Subject to any disclaimer, the term of this patent is extended or adjusted under 35 U.S.C. 154(b) by 968 days.

(21) Appl. No.: 14/408,849

(22) PCT Filed: Jun. 18, 2013

(86) PCT No.: PCT/EP2013/062616
§ 371 (c)(1),
(2) Date: Dec. 17, 2014

(87) PCT Pub. No.: WO2014/009111
PCT Pub. Date: Jan. 16, 2014

(65) Prior Publication Data
US 2016/0158431 A1    Jun. 9, 2016

Related U.S. Application Data

(60) Provisional application No. 61/671,192, filed on Jul. 13, 2012.

(30) Foreign Application Priority Data

Jul. 13, 2012    (SE) .................. 1250826-3

(51) Int. Cl.
*A61M 1/36* (2006.01)
*G01M 3/28* (2006.01)

(52) U.S. Cl.
CPC ........ *A61M 1/3621* (2013.01); *A61M 1/3653* (2013.01); *A61M 1/3656* (2014.02);
(Continued)

(58) Field of Classification Search
CPC .............. A61M 1/3653; A61M 1/3656; A61M 1/3621; A61M 2205/50; A61M 2205/3331; G01M 3/2815
(Continued)

(56) References Cited

U.S. PATENT DOCUMENTS 5,906,589 A    5/1999    Gordon et al.
6,066,261 A    5/2000    Spickermann
(Continued)

FOREIGN PATENT DOCUMENTS

WO    97/10013    3/1997
WO    2009/156174    12/2009
(Continued)

OTHER PUBLICATIONS

Wikipedia, Fourier Transform., Waybackmachine, https://en.wikipedia.org/wiki/Fourier_transform., Dec. 4, 2008.*
(Continued)

*Primary Examiner* — Yoshihisa Ishizuka
(74) *Attorney, Agent, or Firm* — K&L Gates LLP

(57) ABSTRACT

A filtering device receives a pressure signal (P) from a pressure sensor in a fluid containing system, the pressure signal (P) comprising first pulses originating from a first periodic pulse generator and second pulses. The device acquires a reference signal which is indicative of a current operating frequency of the first periodic pulse generator. The device identifies, based on the reference signal, a plurality of harmonics ($\bar{v}_1$-$\bar{v}_8$) associated with the current operating frequency, computes correlation values ($\lambda_1$-$\lambda_8$) between the harmonics and the pressure signal (P) within a time window in the pressure signal (P), and generates a filtered signal by subtracting, as a function of the correlation values ($\lambda_1$-$\lambda_8$), the harmonics from the pressure signal (P). The use of correlation values is a direct, fast, robust and computation-
(Continued)

efficient approach for estimating the signal contribution (d) from first pulses in the pressure signal (P).

21 Claims, 5 Drawing Sheets

(52) U.S. Cl.
CPC .. *G01M 3/2815* (2013.01); *A61M 2205/3331* (2013.01); *A61M 2205/50* (2013.01)

(58) Field of Classification Search
USPC .......................................... 604/4.01; 702/140
See application file for complete search history.

(56) References Cited

U.S. PATENT DOCUMENTS

| | | | |
|---|---|---|---|
| 6,077,443 | A | 6/2000 | Goldau |
| 6,090,048 | A | 7/2000 | Hertz et al. |
| 6,221,040 | B1 | 4/2001 | Kleinekofort |
| 6,585,675 | B1 | 7/2003 | O'Mahony et al. |
| 6,595,942 | B2 | 7/2003 | Kleinekofort |
| 6,623,443 | B1 | 9/2003 | Polaschegg |
| 6,745,630 | B2 | 6/2004 | Gross |
| 6,780,159 | B2 | 8/2004 | Sandler et al. |
| 6,796,955 | B2 | 9/2004 | O'Mahony et al. |
| 6,804,991 | B2 | 10/2004 | Balschat et al. |
| 6,827,698 | B1 | 12/2004 | Kleinekofort |
| 6,899,691 | B2 | 5/2005 | Bainbridge et al. |
| 7,169,352 | B1 | 1/2007 | Felt et al. |
| 7,172,569 | B2 | 2/2007 | Kleinekofort |
| 7,172,570 | B2 | 2/2007 | Cavalcanti et al. |
| 7,462,161 | B2 | 12/2008 | O'Mahony et al. |
| 7,540,851 | B2 | 6/2009 | O'Mahony et al. |
| 7,632,411 | B2 | 12/2009 | Kuroda et al. |
| 7,648,474 | B2 | 1/2010 | Paolini et al. |
| 7,749,184 | B2 | 7/2010 | Cavalcanti et al. |
| 8,152,751 | B2 | 4/2012 | Roger et al. |
| 8,197,431 | B2 | 6/2012 | Bennison |
| 8,348,850 | B2 | 1/2013 | Frinak et al. |
| 8,439,857 | B2 | 5/2013 | Kopperschmidt et al. |
| 8,460,552 | B2 | 6/2013 | Kopperschmidt et al. |
| 8,529,491 | B2 | 9/2013 | Beiriger |
| 8,574,183 | B2 | 11/2013 | Kopperschmidt |
| 2005/0010118 | A1 | 1/2005 | Toyoda et al. |
| 2005/0054295 | A1 | 3/2005 | Moloudi |
| 2008/0108930 | A1 | 5/2008 | Weitzel et al. |
| 2010/0145250 | A1 | 6/2010 | Bene |
| 2010/0234786 | A1 | 9/2010 | Fulkerson et al. |
| 2011/0021967 | A1 | 1/2011 | Heide et al. |
| 2011/0034814 | A1 | 2/2011 | Kopperschmidt |
| 2011/0301472 | A1 | 12/2011 | Grober et al. |
| 2011/0306866 | A1 | 12/2011 | Thys |
| 2012/0271160 | A1 | 10/2012 | Buckberry |
| 2012/0271161 | A1 | 10/2012 | Buckberry |
| 2013/0012861 | A1 | 1/2013 | Zhang |
| 2013/0020237 | A1 | 1/2013 | Wilt et al. |
| 2013/0026098 | A1 | 1/2013 | Haecker et al. |
| 2013/0134077 | A1 | 5/2013 | Wieskotten et al. |

FOREIGN PATENT DOCUMENTS

| | | |
|---|---|---|
| WO | 2009/156175 | 12/2009 |
| WO | 2010/149726 | 12/2010 |
| WO | 2011/080188 | 7/2011 |
| WO | 2011/080189 | 7/2011 |
| WO | 2011/080190 | 7/2011 |
| WO | 2011/080191 | 7/2011 |
| WO | 2011/080194 | 7/2011 |

OTHER PUBLICATIONS

MIT OpenCourseWare "http://ocw.mit.edu"., 6.003 Signals and Systems Fall 2011 (Year: 2011).*
J.Schesser.,Sinusoids., BME 310 Biomedical Computing., Lecture #2 Chapter 2., "https://web.archive.org/web/20060919042009/https://web.njit.edu/~joelsd/Fundamentals/coursework/BME310computingcw2.pdf" (Year: 2006).*
Prosecution history of U.S. Appl. No. 13/001,314 (now U.S. Pat. No. 9,442,036), filed Dec. 23, 2010.
Prosecution history of U.S. Appl. No. 13/380,631 (now U.S. Pat. No. 9,433,356), filed Mar. 16, 2012.
Prosecution history of U.S. Appl. No. 14/129,087 (now U.S. Pat. No. 9,427,513), filed Apr. 11, 2014.
Prosecution history of U.S. Appl. No. 12/988,146 (now U.S. Pat. No. 8,718,957), filed Oct. 15, 2010.
Prosecution history of U.S. Appl. No. 13/000,856 (now U.S. Pat. No. 8,715,216), filed Dec. 22, 2010.
Prosecution history of U.S. Appl. No. 14/270,246 (now U.S. Pat. No. 9,383,288), filed May 5, 2014.
Prosecution history of U.S. Appl. No. 13/519,532, filed Sep. 12, 2012.
Prosecution history of U.S. Appl. No. 14/123,397, filed Dec. 2, 2013.
Prosecution history of U.S. Appl. No. 13/519,483, filed Sep. 13, 2012.
Prosecution history of U.S. Appl. No. 13/519,559, filed Sep. 12, 2012.
Prosecution history of U.S. Appl. No. 14/234,527, filed May 5, 2014.
Prosecution history of U.S. Appl. No. 14/651,730, filed Jun. 12, 2015.
Prosecution history of U.S. Appl. No. 14/777,695, filed Sep. 16, 2015.
Prosecution history of U.S. Appl. No. 14/917,099, filed Mar. 7, 2016.
Prosecution history of U.S. Appl. No. 15/104,861, filed Jun. 15, 2016.
Glover, Jr., "Adaptive Noise Canceling Applied to Sinusoidal Interferences", IEEE Transactions on Acoustics, Speech, and Signal Processing, Dec. 1977, vol. ASSP-25, No. 6, pp. 484-491.
Widrow et al., "Adaptive Noise Cancelling: Principles and Applications", Proceedings of the IEEE, Dec. 1975, vol. 63, No. 12, pp. 1692-1716.
International Search Report and Written Opinion dated Sep. 17, 2013, for related International Appln. No. PCT/EP2013/062616.

* cited by examiner

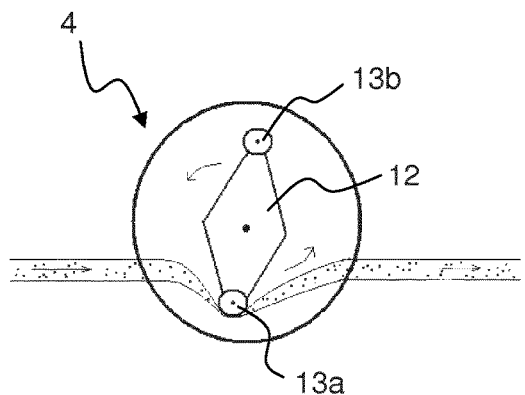
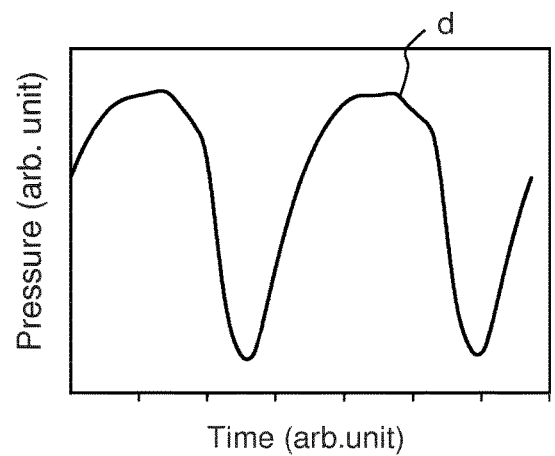
FIG. 3(a)　　　　　　　　　FIG. 3(b)
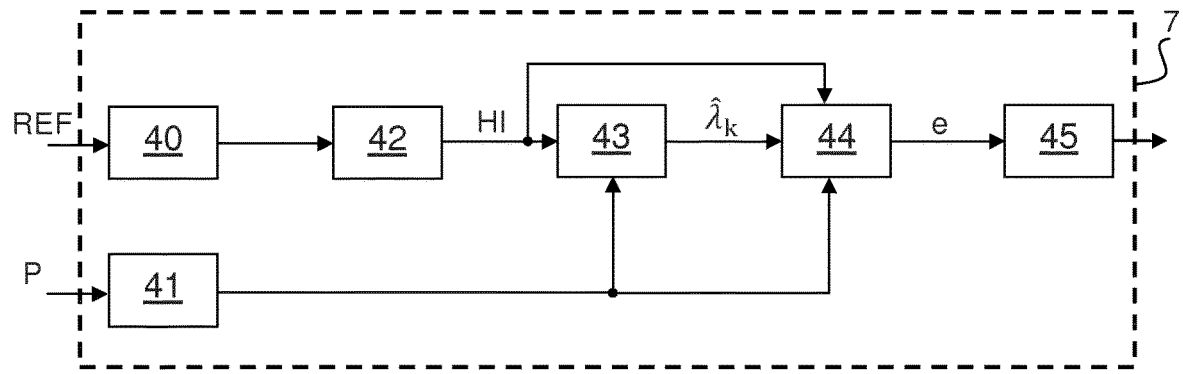
Fig. 4
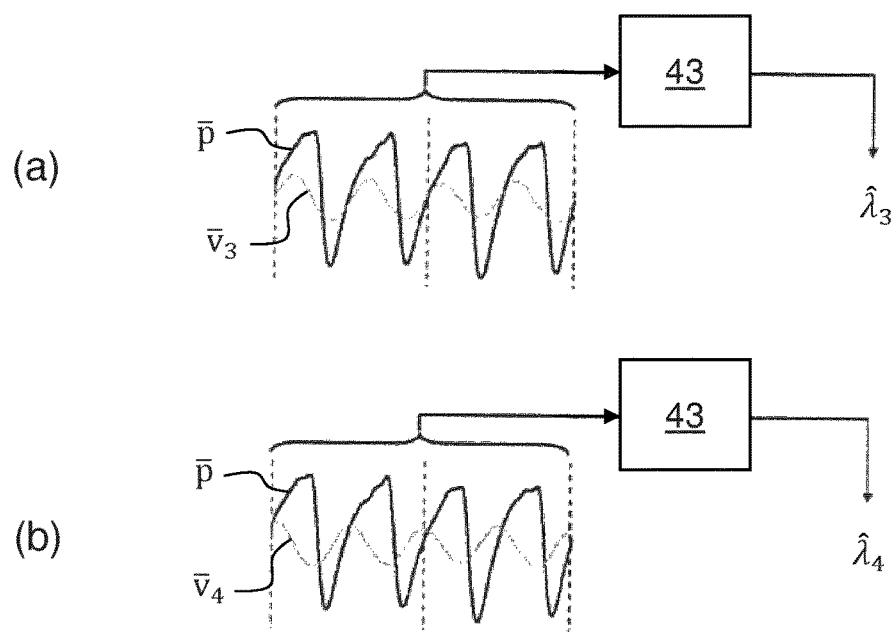
FIG. 5

FILTERING OF PRESSURE SIGNALS FOR SUPPRESSION OF PERIODIC PULSES

CROSS REFERENCE TO RELATED APPLICATIONS

The present application is a National Stage of International Application No. PCT/EP2013/062616, filed on Jun. 18, 2013, which claims priority to Sweden Patent Application No. 1250826-3, filed Jul. 13, 2012, and U.S. Provisional Application No. 61/671,192, filed Jul. 13, 2012, the entire contents of which are being incorporated herein by reference.

TECHNICAL FIELD

The present invention relates to processing of a pressure signal obtained from a pressure sensor in a fluid containing system, and in particular to filtering of the pressure signal for suppression of signal pulses originating from a periodic pulse generator in the fluid containing system. The present invention is e.g. applicable in fluid containing systems for extracorporeal blood treatment.

BACKGROUND ART

In extracorporeal blood processing, blood is taken out of a human subject, processed (e.g. treated) and then reintroduced into the subject by means of an extracorporeal blood flow circuit ("EC circuit") which is part of a blood processing apparatus. Generally, the blood is circulated through the EC circuit by a blood pump. In certain types of extracorporeal blood processing, the EC circuit includes an access device for blood withdrawal (e.g. an arterial needle or catheter) and an access device for blood reintroduction (e.g. a venous needle or catheter), which are inserted into a dedicated blood vessel access (e.g. fistula or graft) on the subject. Such extracorporeal blood treatments include hemodialysis, hemodiafiltration, hemofiltration, plasmapheresis, bloodbanking, blood fraction separation (e.g. cells) of donor blood, apheresis, extracorporeal blood oxygenation, assisted blood circulation, extracorporeal liver support/dialysis, ultrafiltration, etc.

It is vital to minimize the risk for malfunctions in the EC circuit, since these may lead to a potentially life-threatening condition of the subject. Serious conditions may e.g. arise if the EC circuit is disrupted downstream of the blood pump, e.g. by a Venous Needle Dislodgement (VND) event, in which the venous needle comes loose from the blood vessel access. Such a disruption may cause the subject to be drained of blood within minutes. WO97/10013, US2005/0010118, WO2009/156174, WO2010/149726 and US2010/0234786 all propose various techniques for detecting a VND event by identifying an absence of heart or breathing pulses in a pressure signal from a pressure sensor ("venous pressure sensor") on the downstream side of the blood pump in the EC circuit.

Recently, it has also been shown to be possible to monitor and analyze the behavior of physiological pressure generators such as the heart or respiratory system, based on pressure recordings in the EC circuit. Various applications are found in WO2010/149726, WO2011/080189, WO2011/080190, WO2011/080191, WO2011/080194 which are incorporated herein by reference. For example, these applications include monitoring a subject's heart pulse rate, blood pressure, heart rhythm, cardiac output, blood flow rate through the blood vessel access ("access flow"), arterial stiffness, as well as identifying signs of stenosis formation within the blood vessel access, predicting rapid symptomatic blood pressure decrease and detecting, tracking and predicting various breathing disorders.

Furthermore, WO2011/080188 proposes a technique for identifying and signaling a reverse placement of the devices for blood withdrawal and blood reintroduction in the vascular access by detecting and analyzing physiological pulses in a pressure signal recorded in the EC circuit.

All of these monitoring techniques presume that the physiological pulses can be reliably detected in the pressure signal. To enable monitoring, it may be necessary to filter the pressure signal for removal or suppression of signal interferences. The signal interferences comprise pressure pulses ("pump pulses") originating from the blood pump, and may also comprise further interfering pressure pulses, e.g. caused by further pumps, valves, balancing chambers, etc in the EC circuit. It may be a challenging task to properly remove e.g. the pump pulses, since the rate of the physiological pulses and the rate of the blood pump, i.e. the blood flow through the EC circuit, may change over time. If the rate of physiological pulses matches the rate of pump pulses, it is not unlikely that the filtering will remove also the physiological pulses, causing the monitoring technique to fail. Filtering is also rendered difficult by the fact that the pump pulses generally are much stronger than the physiological pulses in the pressure signal.

To address these problems, WO2009/156175 proposes that the pressure signal is filtered in the time-domain, by subtraction of a predicted signal profile of the pressure pulses originating from the blood pump. The predicted signal profile may be obtained by reference measurements or by simulations. In one implementation, the predicted signal profile is retrieved from a library of pre-stored reference profiles, based on the current operating frequency of the blood pump, and subtracted from the pressure signal, based on timing information given by a dedicated pump sensor or by a control signal for the blood pump. In another implementation, the predicted signal profile is retrieved and subtracted by a best match technique, in which the predicted signal profile is scaled and shifted so as to minimize differences to the pressure signal before the subtraction. In yet another implementation, the predicted signal profile and the pressure signal are input to an adaptive filter that iterates to generate an error signal which is essentially free of the signal interferences caused by the blood pump.

WO97/10013 proposes a different filtering technique denoted "notch-equivalent filter", which presumes that the frequency and phase of the blood pump are known. Sinus signals are generated at the known frequency and at multiples of the known frequency. The sinus signals are input to an adaptive filter, which adapts the amplitude and the phase of each sinus signal to the pressure signal to be filtered. The sinus signals are then subtracted from the pressure signal at the respective amplitude and phase.

There is a continued need to achieve an improved filtering technique, in terms of one or more of the following: ability to handle overlap in frequency and/or time between pump pulses and physiological pulses, complexity of the filtering technique, ability to generate the filtered signal in real time, processing efficiency and memory usage during filtering, accuracy of the filtered signal, and robustness of the filtering technique.

Corresponding needs may arise in other fields of technology. Thus, generally speaking, there is a need for an improved technique for filtering a time-dependent pressure signal obtained from a pressure sensor in a fluid containing system so as to essentially remove first pulses originating from a first periodic pulse generator in the fluid containing system while retaining second pulses of other origin.

SUMMARY

It is an objective of the invention to at least partly overcome one or more limitations of the prior art.

Another objective is to provide a filtering technique capable of meeting one or more of the above-mentioned needs.

One or more of these objectives, as well as further objectives that may appear from the description below, are at least partly achieved by devices for filtering a pressure signal, a method of filtering a pressure signal and a computer-readable medium according to the independent claims, embodiments thereof being defined by the dependent claims.

A first aspect of the invention is a device for filtering a pressure signal obtained from a pressure sensor in a fluid containing system, the pressure signal comprising first pulses originating from a first periodic pulse generator and second pulses. The device comprises: an input for receiving the pressure signal from the pressure sensor, and a signal processor connected to the input. The signal processor is configured to: identify, based on a reference signal which is indicative of a current operating frequency of the first periodic pulse generator, a plurality of harmonics associated with the current operating frequency; compute correlation values between the harmonics and the pressure signal within a time window in the pressure signal; and generate a filtered signal by subtracting, as a function of the correlation values, the harmonics from the pressure signal.

It is realized that since the first pulses are generated by a periodic pulse generator, i.e. periodically, the energy of one or more first pulses within the time window will be distributed over a set of harmonic frequencies. Each harmonic frequency is a component frequency that is an integer multiple of a fundamental frequency of the periodic pulse generator, which may but need not be equal to the current operating frequency. In any event, the set of harmonic frequencies are identifiable based on the current frequency.

The first aspect capitalizes on this insight to define a filtering technique which is inherently matched to the pulse generation process in the first periodic pulse generator, since the filtering technique operates by subtracting harmonics that are identified based on the reference signal, which represents the current operating frequency of the first periodic pulse generator. The reference signal may be a separate signal which is received by the signal processor via a second input of the device, e.g. in the form of a pulse signal from a tachometer or the like associated with the first periodic pulse generator, a control signal for the first periodic pulse generator, or a secondary pressure signal from another pressure sensor in or associated with the fluid containing system. Alternatively, the pressure signal itself may be used as the reference signal.

The first aspect is also based on the insight that the energy content (amplitude) and phase of each harmonic frequency in the one or more first pulses within the time window may be estimated by correlating the pressure signal with a respective harmonic, i.e. a sinusoid at the respective harmonic frequency. The resulting correlation value thereby defines a "weight" of the harmonic in the pressure signal, similar to an eigenvalue, which may be applied when subtracting the harmonic from the pressure signal. Thus, in contrast to prior art approaches using adaptive filters, which are iterative by nature, the first aspect provides a direct approach of determining signal contributions to be subtracted from the pressure signal for the purpose of eliminating or at least significantly suppressing the first pulses. Thus, in contrast to approaches using adaptive filters, the inventive filtering technique has no stability or convergence issues, e.g. after a change in operating frequency for the first periodic pulse generator.

Furthermore, the filtering technique of the first aspect may obviate the need to store a library of reference profiles. It should be noted that the computation of the correlation values between the harmonics and the pressure signal is a fairly simple operation, which may be efficiently implemented in either hardware or software, or a combination of hardware and software. Thus, the first aspect involves a fast and accurate technique of estimating the contribution of each harmonic to the first pulse(s) within the time window. For example, each correlation value may be obtained as a simple scalar product (dot product) between two vectors.

In one embodiment, the plurality of harmonics comprises sine waves at a plurality of harmonic frequencies and cosine waves at said plurality of harmonic frequencies.

In one embodiment, the signal processor is configured to, when computing the correlation value of a given harmonic, generate product values by multiplying individual pressure values in the pressure signal by individual values in the given harmonic, and generate the correlation value as a function of a time-sequence of the product values.

In one embodiment, the signal processor is configured to select the time-sequence of product values to correspond to at least one period of the given harmonic, and preferably at least two periods of the given harmonic.

In one embodiment, the signal processor is configured to select the time-sequence of product values to match a whole number of periods of the given harmonic.

In one embodiment, the signal processor is configured to, when computing the correlation values, set all harmonics among the plurality of harmonics to a length that matches the time window. Phrased differently, the signal processor may be configured to select the time sequence of product values to match the time window in the pressure signal for all harmonics among the plurality of harmonics.

In one embodiment, the signal processor is configured to generate the correlation value as a summation, weighted or non-weighted, of the time-sequence of product values.

In one embodiment, the signal processor is configured to operate a low-pass filter on the time-sequence of product values, and obtain the correlation value of the given harmonic based on an output signal of the low-pass filter.

In an alternative embodiment, the signal processor is configured to obtain a signal vector that represents the pressure signal within the time window, obtain a harmonic vector that represents a given harmonic, compute a scalar product between the signal vector and the harmonic vector, and obtain the correlation value based on the scalar product. For example, the signal processor may be configured to generate all correlation values based on the same signal vector.

In one embodiment, each of the harmonics is set to have an energy of 1 within the time window.

In one embodiment, the signal processor is further configured to, before computing the correlation values, process the pressure signal for selective removal of frequencies outside a predefined frequency range associated with the second pulses, and wherein the signal processor is configured to limit the plurality of harmonics to the predefined frequency range.

In one embodiment, the signal processor is configured to generate the filtered signal by combining the harmonics as a function of the correlation values so as to form a predicted temporal signal profile of the first pulses within the time window, and subtracting the predicted temporal profile from the pressure signal.

In one embodiment, the signal processor is configured to generate the filtered signal by subtracting a linear combination of the harmonics using the correlation values as coefficients.

In one embodiment, the signal processor is configured to generate the filtered signal by subtracting the harmonics from the pressure signal within the time window.

In one embodiment, the signal processor is configured to repeatedly generate the filtered signal for a sequence of time windows so as to essentially eliminate the first pulses while retaining the second pulses. In one implementation, the time windows in the sequence of time windows are non-overlapping. In another implementation, the time windows in the sequence of time windows are partially overlapping, wherein each subtraction of the harmonics from the pressure signal within the time window of the pressure signal results in a filtered signal segment, said signal processor being further configured to generate the filtered signal by combining overlapping signal values in the filtered signal segments.

In one embodiment, the fluid containing system comprises an extracorporeal blood flow circuit connected to a blood system in a human body, and wherein the first periodic pulse generator comprises a pumping device in the extracorporeal blood flow circuit, and wherein the second pulses originates from a physiological pulse generator in the human body.

A second aspect of the invention is a device for filtering a pressure signal obtained from a pressure sensor in a fluid containing system, the pressure signal comprising first pulses originating from a first periodic pulse generator and second pulses. The device comprises: means for receiving the pressure signal from the pressure sensor; means for identifying, based on a reference signal which is indicative of a current operating frequency of the first periodic pulse generator, a plurality of harmonics associated with the current operating frequency; means for computing correlation values between the harmonics and the pressure signal within a time window in the pressure signal; and means for generating a filtered signal by subtracting, as a function of the correlation values, the harmonics from the pressure signal.

A third aspect of the invention is a method of filtering a pressure signal obtained from a pressure sensor in a fluid containing system, the pressure signal comprising first pulses originating from a first periodic pulse generator and second pulses. The method comprises the steps of: obtaining the pressure signal from the pressure sensor; identifying, based on a reference signal which is indicative of a current operating frequency of the first periodic pulse generator, a plurality of harmonics associated with the current operating frequency; computing correlation values between the harmonics and the pressure signal within a time window in the pressure signal; and generating a filtered signal by subtracting, as a function of the correlation values, the harmonics from the pressure signal.

A fourth aspect of the invention is a computer-readable medium comprising computer instructions which, when executed by a processor, cause the processor to perform the method of the third aspect.

Any one of the above-identified embodiments of the first aspect may be adapted and implemented as an embodiment of the second to fourth aspects.

Still other objectives, features, aspects and advantages of the present invention will appear from the following detailed description, from the attached claims as well as from the drawings.

BRIEF DESCRIPTION OF DRAWINGS

Embodiments of the invention will now be described in more detail with reference to the accompanying schematic drawings.

FIG. 3(a) is a side view of a rotor of a peristaltic pump, and FIG. 3(b) is a plot of pressure pulses generated during a full rotation of the rotor in FIG. 3(a), as measured by a pressure sensor in the extracorporeal blood processing apparatus of FIG. 1.

FIG. 4 is a block diagram of a filtering device according to one embodiment.

FIGS. 5(a)-5(b) illustrate generation of correlation values for a given harmonic frequency, by correlation with a sine wave and a cosine wave, respectively.

DETAILED DESCRIPTION OF EXAMPLE EMBODIMENTS

Figure 1:
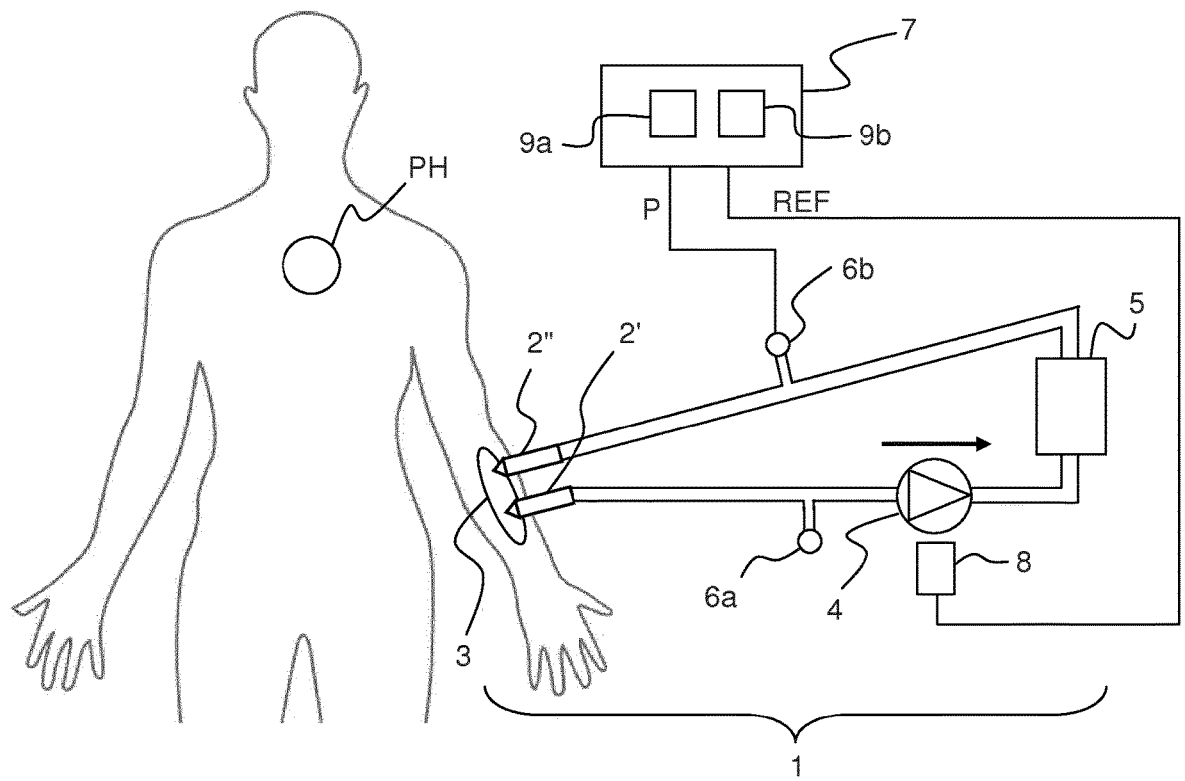
FIG. 1 a schematic diagram of a blood path in an extracorporeal blood processing apparatus attached to a human subject.

Throughout the description, the same reference numerals are used to identify corresponding elements.

FIG. 1 illustrates a human subject which is connected to an extracorporeal fluid circuit 1 by way of access devices 2', 2" inserted into a dedicated vascular access 3 (also known as "blood vessel access") on the subject. The extracorporeal fluid circuit 1 (denoted "EC circuit" in the following) is configured to communicate blood to and from the cardiovascular system of the subject. In one example, the EC circuit 1 is part of an apparatus for blood processing, such as a dialysis machine. In the illustrated example, a blood pump 4 draws blood from the vascular access 3 via access device 2' and pumps the blood through a blood processing unit 5, e.g. a dialyzer, and back to the vascular access 3 via access device 2". Thus, when both access devices 2', 2" are connected to the vascular access 3, the EC circuit 1 defines a blood path that starts and ends at the vascular access 3. The EC circuit 1 may be seen to comprise a "venous side" which is the part of the blood path located downstream of the blood pump 4, and an "arterial side" which is the part of the blood path located upstream of the pump 4.

Pressure sensors 6a and 6b are arranged to detect pressure waves in the EC circuit 1. As used herein, a "pressure wave" is a mechanical wave in the form of a disturbance that travels or propagates through a material or substance. In the context of the following examples, the pressure waves propagate in the blood in the cardiovascular system of the subject and in the blood path of the EC circuit 1 at a velocity that typically lies in the range of about 3-20 m/s. The sensors 6a, 6b, which are in direct or indirect hydraulic contact with the blood, generates pressure data that forms a pressure pulse for each pressure wave. A "pressure pulse" is thus a set of data samples that define a local increase or decrease (depending on implementation) in signal magnitude within a time-dependent measurement signal ("pressure signal") P.

Figure 2:
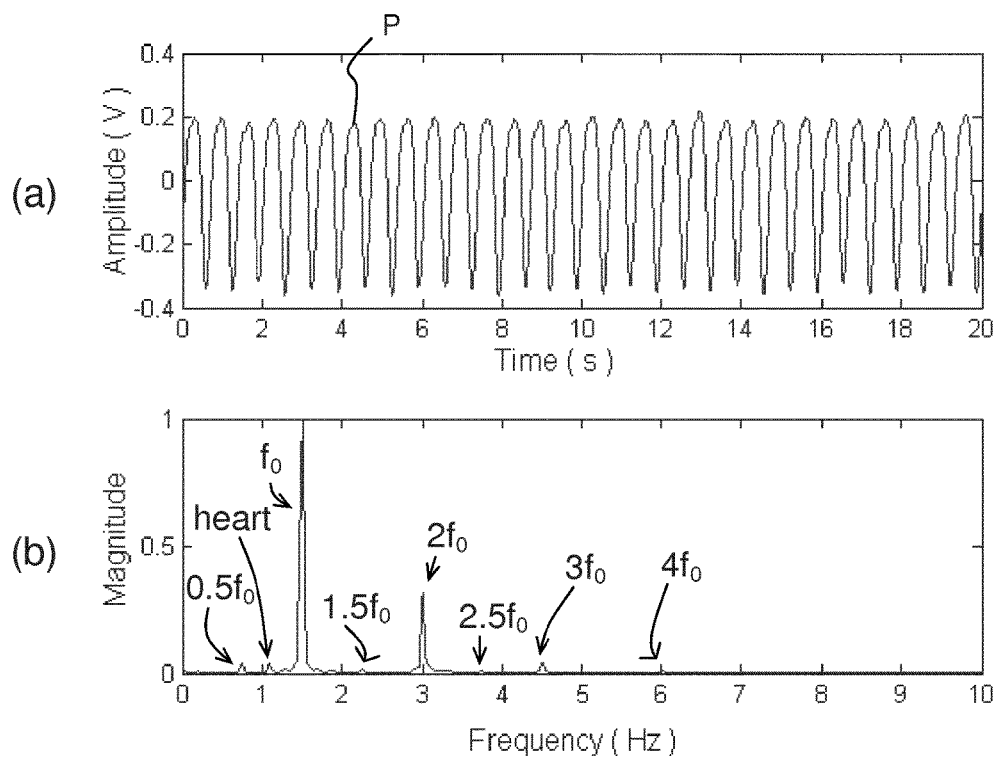
FIG. 2(a) is a plot in the time domain of a pressure signal containing both pump frequency components and a heart signal.
FIG. 2(b) is a plot of the corresponding signal in the frequency domain.

FIG. 2(a) shows an example of a time-resolved pressure signal P acquired from sensor 6b, and FIG. 2(b) shows the corresponding spectral density, i.e. signal energy as a function of frequency. The spectral density reveals that the pressure signal P contains frequency components that emanate from and are given by the design of the blood pump 4. As seen, the frequency components are a set of harmonic frequencies $0.5f_0$, $f_0$, $1.5f_0$, $2f_0$, etc. In the illustrated example, the blood pump 4 is a rotary peristaltic pump of the type indicated in FIG. 3(a), and the frequency components are governed by the revolution of the rotor 12 and the engagement of the rollers 13a, 13b with the tube segment. The dominating frequency $f_0$ is the pumping frequency, i.e. the frequency of pump strokes, with each pump stroke being generated by the engagement of one of the rollers 13a, 13b with the tube segment. FIG. 3(b) illustrates the pressure pulsations ("pump pulses", d) in the pressure signal that originate exclusively from the pump 4 during one revolution of the rotor 12. Thus, the pump pulses d in FIG. 3(b) represent the pressure waves that are generated by the rollers 13a, 13b engaging the tube segment during a full rotor revolution. Returning to FIGS. 2(a)-2(b), the pressure signal P also includes pressure pulsations ("heart pulses") that originate from the beating of the heart in the patient. In this example, the heart pulses are much weaker than the pump pulses and are difficult to detect in the pressure signal P, which is dominated by the pump pulses. Generally, the pressure signal P may contain pressure pulses ("physiological pulses") from any physiological pulse generator PH (FIG. 1), periodic or non-periodic, in the patient, including reflexes, voluntary muscle contractions, non-voluntary muscle contractions, the heart, the breathing system, the autonomous system for blood pressure regulation and the autonomous system for body temperature regulation.

In the illustrated example, a filtering device 7 is connected to the sensor 6b by a transmission line to acquire and process the pressure signal P, for the purpose of eliminating or at least significantly suppressing the pump pulses while retaining physiological pulses originating from one or more of the above-mentioned physiological pulse generators. The device 7 is also connected to receive a reference signal REF, which is generated by a reference sensor 8 to indicate the current operating frequency of the pump 4. In one example, the reference sensor 8 is a tachometer associated with the pump 4 (as shown) to measure the rotation speed of an element (e.g. the rotor 12) in the power transmission of the pump 4. Such a tachometer may be configured to provide any number of readings representative of the rotation speed during each rotor revolution, e.g. at a single instance or at plural instances during each rotor revolution. In another example, the reference signal REF is a control signal for the pump 4, e.g. indicating a set value for the blood flow rate or the pumping frequency of the pump 4, or indicating the current/ power fed to a motor that drives the pump 4. In another example, the reference signal REF is a pressure signal generated by another pressure sensor in the EC circuit 1 (e.g. the sensor 6a) which is arranged to detect pressure waves originating from the pump 4. In yet another example, the pressure signal P to be filtered is used as the reference signal REF. There are many techniques, well known to the skilled person, for determining the current operating frequency of the pump 4 from any one of these types of reference signals.

Although not shown herein, it is to be understood that the device 7 may instead be connected to suppress pump pulses in a pressure signal from sensor 6a, or in pressure signals from more than one pressure sensor in the EC circuit 1.

Depending on implementation, the device 7 may use digital components or analog components, or a combination thereof, for acquiring and processing the pressure signal. The device 7 may be a computer, or a similar data processing device, with adequate hardware for acquiring and processing the pressure signal in accordance with different embodiments of the invention. Embodiments of the invention may e.g. be implemented by software instructions that are supplied on a computer-readable medium for execution by a processor 9a in conjunction with an electronic memory 9b in the device 7. The computer-readable medium may be a tangible product (e.g. magnetic medium, optical disk, read-only memory, flash memory, etc) or a propagating signal.

The device 7 is designed based on the insight that it is possible to directly estimate the frequency content of the pump pulses by straight-forward correlation operations if the harmonic frequencies of the pump 4 are (approximately) known.

In one embodiment, shown in FIG. 4, the device 7 comprises an input block 40 for acquiring the reference signal REF and an input block 41 for acquiring the pressure signal P. The input blocks 40, 41 may be implemented by different signal ports of an I/O interface of the device 7. The input blocks 40, 41 may also be configured to pre-process the signals REF and P, e.g. for AD conversion, signal amplification, removal of offset, high frequency noise and supply voltage disturbances, etc. The reference signal REF is supplied to a harmonics detector 42, which processes the reference signal to identify the current harmonic frequencies generated by the pump 4. The skilled person realizes that it may be sufficient to identify one harmonic frequency in the reference signal REF for all harmonic frequencies to be known, as long as it can be determined which one of the available harmonic frequencies that has been identified. The information HI about the current harmonic frequencies is supplied to a correlator 43, which is configured to compute a respective correlation value $\hat{\lambda}_k$ between the pressure signal P, received via the input block 41, and a set of harmonics at the different harmonic frequencies given by the information HI. Each harmonic is a sinusoid at a given harmonic frequency. The resulting correlation values $\hat{\lambda}_k$ and the information HI are supplied to a subtraction block 44, which is configured to subtract a linear combination of harmonics from the pressure signal P using the correlation values as coefficients. The linear combination may be seen to form a current estimation $\hat{d}$ of the pump pulses d (cf. FIG. 3(b)) in the pressure signal P, and the subtraction block 44 thus produces a filtered signal e in which the pump pulses are eliminated/suppressed. The filtered signal e is then output by an output block 45, which also may be part of the above-mentioned I/O interface.

It is realized that the filtered signal e may be further processed, by device 7 or a separate device, for any type of monitoring purpose, e.g. as described in the Background section. Such monitoring purposes include monitoring the integrity of the connection between the EC circuit 1 and the patient, e.g. with respect to VND or proper placement of the access devices 2', 2", and monitoring/analyzing the behavior of physiological generators PH in the patient, such as the heart or the respiratory system.

In one embodiment, the correlator 43 is configured to generate the correlation values for individual time windows in the pressure signal P. For each time window, the correlator 43 obtains a pressure vector $\bar{p}$ that represents a time sequence of N pressure values of the pressure signal P within the time window:

$$\bar{p} = \begin{bmatrix} p1 \\ p2 \\ \vdots \\ pN \end{bmatrix}$$

and L different harmonic vectors $\bar{v}_k$ with N signal values each, $$\bar{v}_k = \begin{bmatrix} v_k 1 \\ v_k 2 \\ \vdots \\ v_k N \end{bmatrix}$$

$$k = 1, 2, \ldots, L.$$

Each harmonic vector $\bar{v}_k$ corresponds to one of the above-mentioned harmonics and its signal values define a sinusoid at one of the current harmonic frequencies (given by HI). Specifically, for reasons to be explained in more detail below, the harmonic vectors $\bar{v}_k$ are obtained to contain one sine wave and one cosine wave at each current harmonic frequency.

In one embodiment, which facilitates the subsequent processing by the subtraction block 44, the harmonic vectors $\bar{v}_k$ are furthermore obtained to have the property:

$$\bar{v}_i^T \bar{v}_j = \begin{cases} 1, & i = j \\ 0, & i \neq j \end{cases} \quad (1)$$

which means that the energy of each harmonic vector $\bar{v}_k$ is equal to one (1) and that the different harmonic vectors $\bar{v}_k$ are uncorrelated (within the time window). The correlation value $\hat{\lambda}_k$ for such a harmonic vector $\bar{v}_k$ may be computed by processing efficient vector multiplication (i.e. as a dot product) between the harmonic vector $\bar{v}_k$ and the pressure vector $\bar{p}$ according to:

$$\hat{\lambda}_k = \bar{v}_k^T \bar{p} \quad k=1,2,\ldots,L. \quad (2)$$

Thus, each correlation value $\hat{\lambda}_k$ is given by a summation of a time series of product values formed by multiplying individual pressure values in the pressure vector $\bar{p}$ by individual signal values in the harmonic vector $\bar{v}_k$. The subtraction block 44 may then use the correlation values $\hat{\lambda}_k$ to generate a filtered signal vector $\bar{e}$, $$\bar{e} = \begin{bmatrix} e1 \\ e2 \\ \vdots \\ eN \end{bmatrix}$$

by subtracting a current estimation $\hat{d}$ of the pump pulses from the pressure vector $\bar{p}$:

$$\bar{e} = \bar{p} - \hat{d} \quad (3)$$

where the current estimation $\hat{d}$ is generated as a linear combination of the harmonic vectors $\bar{v}_k$ using the correlation values $\hat{\lambda}_k$ as coefficients:

$$\hat{d} = \sum_{k=1}^{L} \hat{\lambda}_k \bar{v}_k \quad (4)$$

In this embodiment, the correlation values $\hat{\lambda}_k$ are generated and applied for subtraction with respect to the same time window. Thereby, the resulting linear combination of harmonic vectors $\bar{v}_k$ is likely to adequately mimic the pump pulses and result in proper filtering. However, it is conceivable to implement the correlator 43 to compute the correlation values $\hat{\lambda}_k$ in one time window, and the subtraction block 44 to apply these correlation values $\hat{\lambda}_k$ for subtraction in one or more subsequent time windows in the pressure signal P.

It should be noted that the correlator 43 may be implemented to use harmonic vectors $\bar{v}_k$ with an energy that differs from 1. However, such embodiments require modification of Eq. (2) and/or Eq. (4) and may potentially increase the computational load on the device 7.

As noted above, the harmonic vectors $\bar{v}_k$ are obtained to include both a sine wave and a cosine wave at each harmonic frequency. As an example, FIG. 5(*a*) illustrates the computation of the correlation value $\hat{\lambda}_3$ for a sine wave $\bar{v}_3$ at frequency $f_0$, and FIG. 5(*b*) illustrates the computation of the correlation value $\hat{\lambda}_4$ for a cosine wave $\bar{v}_4$ at frequency $f_0$. The use of both sine and cosine waves automatically brings the linear combination of harmonic vectors $\bar{v}_k$ to be correctly matched to the current phase of the pump. This technical advantage may be understood by considering that the linear combination of a sine wave and a cosine wave is equivalent to a sine wave with a modified amplitude and phase, e.g. with respect to FIG. 5:

$$\hat{\lambda}_3 \sin(2\pi f_0 t) + \hat{\lambda}_4 \cos(2\pi f_0 t) = \sqrt{(\hat{\lambda}_3^2 + \hat{\lambda}_4^2)} \sin(2\pi f_0 t + \theta)$$

with $$\theta = \arctan\left(\frac{\hat{\lambda}_4}{\hat{\lambda}_3}\right).$$

In an alternative embodiment, the correlation values are only computed for one of a sine wave and a cosine wave at each harmonic frequency, but this requires the subtraction block 44 and/or the correlator 43 to compute, estimate or otherwise obtain a proper phase angle θ for each harmonic frequency. For example, the subtraction block 44 and/or the correlator 43 may be configured to obtain the respective phase angle by cross-correlating the sine wave (or the cosine wave, as the case may be) at each harmonic frequency with the pressure vector $\bar{p}$, where the phase angle is given by the relative displacement of the sine wave at maximum correlation and the amplitude is given by the maximum correlation. It is understood that an embodiment that determines the phase angle in this way involves significantly more correlation operations than an embodiment that correlates a sine wave and a cosine wave to the pressure vector according to Eq. (2).

Figure 6:
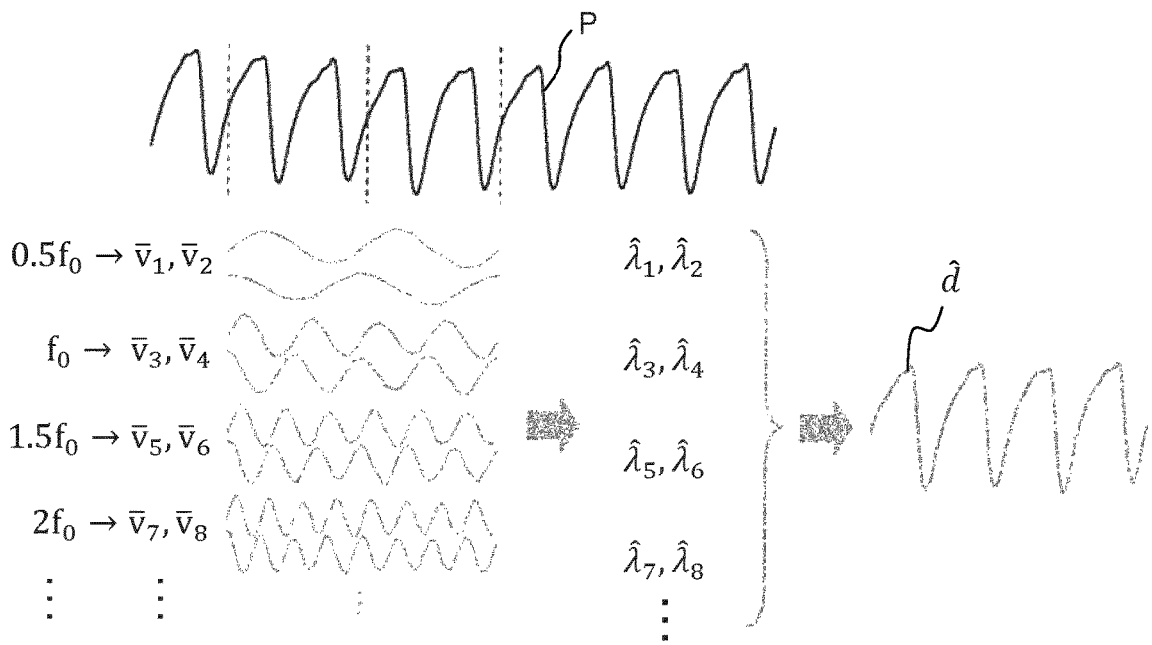
FIGS. 6-7 illustrate a sequence of events when generating a pump profile based on a pressure signal segment corresponding to two and four full rotations of the blood pump, respectively.
Figure 7:
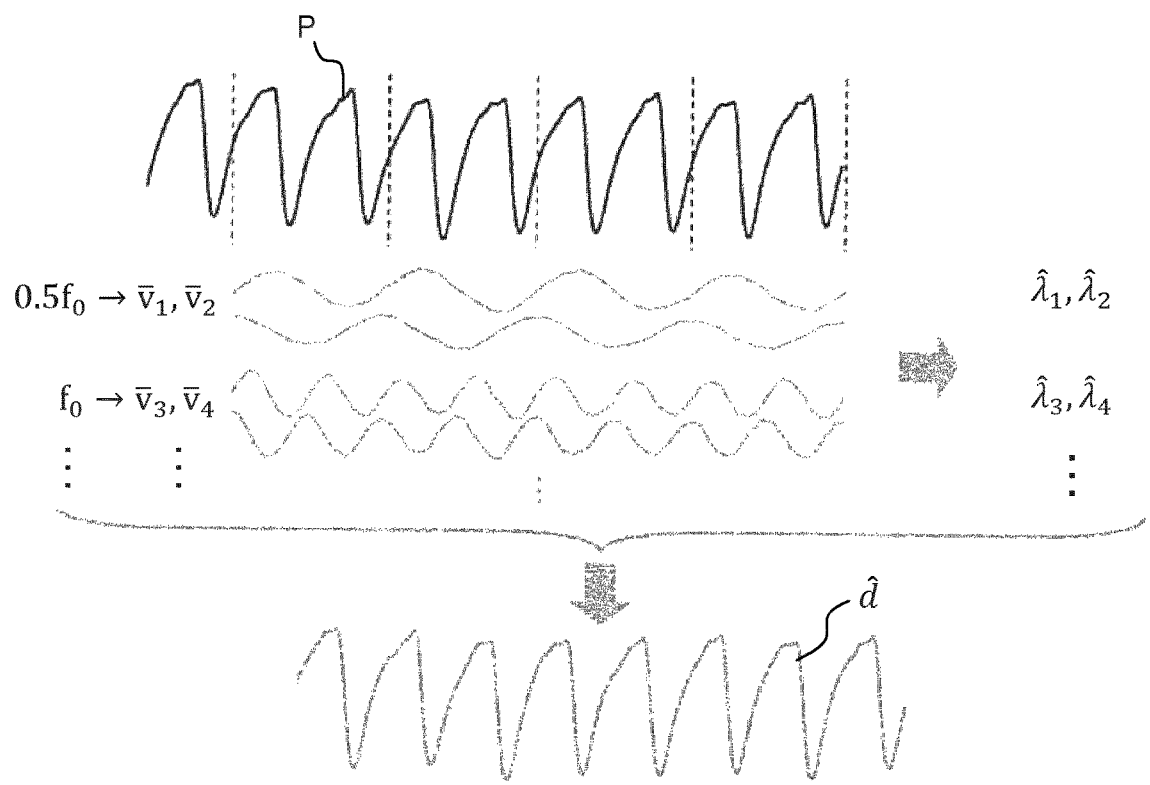

As noted above, the harmonic vectors $\bar{v}_k$ should be uncorrelated for optimum performance. This basically means that each harmonic vector $\bar{v}_k$ should contain a whole number of periods. For computation efficiency, it may be desirable that all correlation values $\hat{\lambda}_k$ are computed in relation to the same pressure vector $\bar{p}$, i.e. within the same time window in the pressure signal P. This in turn means that the time window should match a whole number of periods of the smallest harmonic frequency, which is $0.5f_0$ in FIG. 2(b) and in the following examples. The skilled person realizes that the accuracy of the correlation values is improved with increasing length of the time window (increasing number of periods). However, as the time window is increased, so is the computational load and the time required to produce the filtered signal vector $\bar{e}$. While it is possible to match the time window to a single period of the smallest harmonic frequency, a preferable trade-off between accuracy and time delay may be achieved when the time window is matched to a number of periods in the range of 2-10, and preferably 2-6 periods of the smallest harmonic frequency. As an example, FIG. 6 illustrates a computation of correlation values for sine and cosine waves $\bar{v}_1$-$\bar{v}_8$ at frequencies $0.5f_0$, $f_0$, $1.5f_0$ and $2f_0$ within a time window matched to 2 periods at $0.5f_0$. FIG. 7 illustrates a corresponding computation when the time window is matched to 4 periods at $0.5f_0$. FIGS. 6-7 also indicate that the harmonic vectors may be combined using the correlation values to form an estimated or predicted temporal pump profile $\hat{d}$ within the respective time window.

Figure 8:
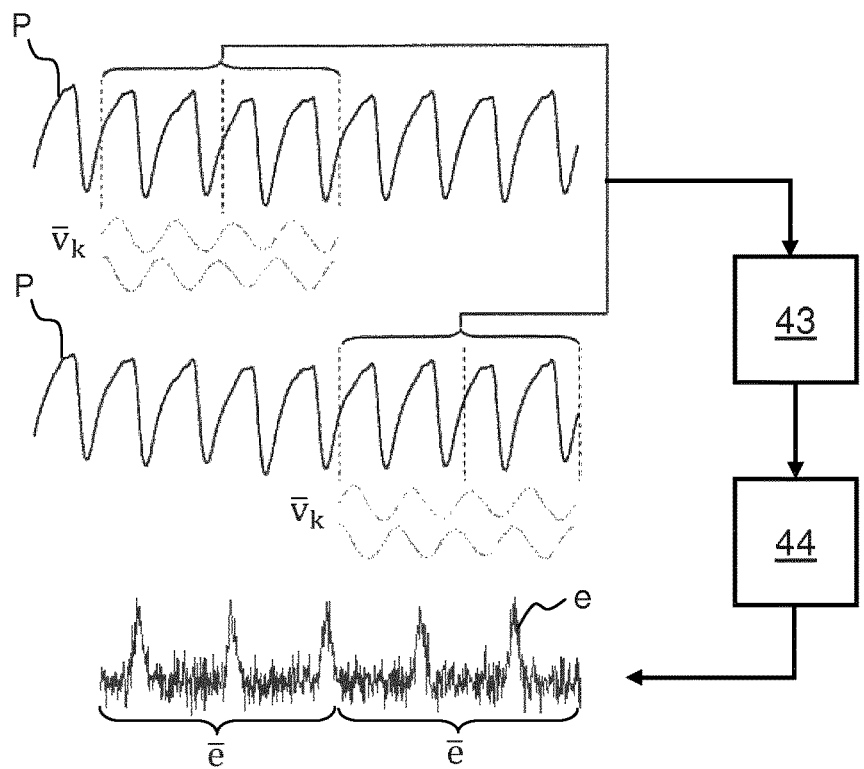
FIGS. 8-9 illustrate generation of a filtered signal based on non-overlapping and overlapping pressure signal segments, respectively.

In one embodiment, which is exemplified in FIG. 8, the consecutive time windows are selected to be non-overlapping in the pressure signal P. Since each time window results in a filtered signal vector $\bar{e}$, the filtered signal e is formed by the resulting time sequence of filtered signal vectors $\bar{e}$. This embodiment puts low computation load on the device 7.

Figure 9:
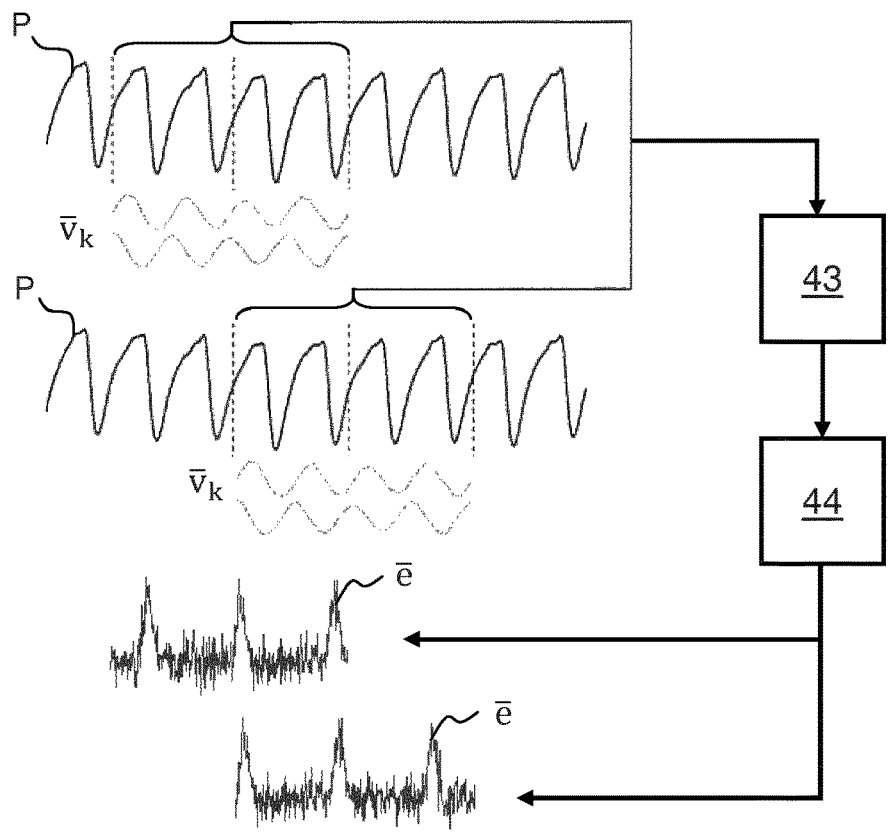

In another embodiment, which is exemplified in FIG. 9, the consecutive time windows are selected to overlap in the pressure signal P. Like in FIG. 8, each time window results in a filtered signal vector $\bar{e}$, but the filtered signal e is generated by combining the overlapping portions of the filtered signal vectors $\bar{e}$, e.g. by computing an element-wise average within the overlapping portions. Combining the overlapping portions will improve the quality of the filtered signal e, albeit at the cost of increased computational load.

As understood from FIGS. 5-9, it is desirable for the signal values $v_k1$, $v_k2$, etc in each harmonic vector $\bar{v}_k$ to have the same locations within the time window as the pressure values p1, p2, etc in the pressure vector $\bar{p}$. For computational efficiency, it may be desirable that the harmonic vectors $\bar{v}_k$ are pre-defined for a nominal set of harmonic frequencies and stored as templates in computer memory (cf. 9b in FIG. 1). Thereby, the harmonic vectors $\bar{v}_k$ have fixed signal values at given locations within each time window, and these locations are preferably the same for all pre-defined harmonic vectors $\bar{v}_k$. Since the pumping frequency may change over time, the input block 41 (FIG. 4) may be configured to generate the pressure values in temporal alignment with the signal values in the pre-defined harmonic vectors. In one such embodiment, denoted "synchronous sampling" herein, input block 41 is configured to sample the pressure values synchronously with the motion of the pump revolutions, i.e. at the same respective locations along the circle spanned by the rollers 13a, 13b of the pump 4 (FIG. 3(a)). The synchronous sampling may be controlled based on the reference signal REF, which is acquired by input block 40. In another embodiment, denoted "synchronous re-sampling" herein, input block 41 is configured to sample the pressure values without (or with insufficient) synchronization with the pump rotation and then adjust the time scale by subjecting the sampled pressure values to a re-sampling that generates pressure values at a respective given timing (location) within each time window using interpolation among the sampled pressure values. The synchronous re-sampling may also be controlled based on the reference signal REF. In yet another embodiment, input block 41 may be configured to sample the pressure signal P at such a high sample rate that there is always (i.e. for all pumping frequencies) an approximate match between a pressure value in the pressure vector and a signal value in the harmonic vectors. Thereby, the pressure vector may be formed by selecting a best match among the sampled pressure values for each location in the time window.

In an alternative, the device 7 is configured to store a respective set of harmonic vectors for a plurality of pumping frequencies, such that the signal values in the harmonic vectors are aligned with the sampled pressure values at the respective pumping frequency. In another alternative, the harmonic vectors are computed on the fly (by processor 9a), by operating standard trigonometric functions that produce a sine wave and/or a cosine wave at the current harmonic frequencies, such that the signal values in the harmonic vectors are aligned with the sampled pressure values.

Generally, to prevent aliasing effects, it may be preferable that input block 41 is configured to apply a low-pass filter to the pressure signal before the sampling to avoid including frequencies which are higher than half the sampling frequency.

In a further embodiment, input block 41 may be configured to apply a low-pass, band-pass or high-pass filter, or any combination thereof, so as to selectively transmit a limited frequency range associated with the physiological pulses to be isolated in the pressure signal. This will limit the range of frequencies present in the signal supplied to the correlator 43 and the subtraction block 44, and thereby reduce the computational load. For example, the correlator 43 only needs to compute the correlation values for the harmonic frequencies that fall within the limited frequency range. Also, since the number of correlation values and harmonic vectors are reduced, the computational load in subtraction block 44 is likewise reduced. The limited frequency range may e.g. be set to approx. 0.5-3 Hz if the physiological pulses originate from the heart, approx. 0.15-0.4 Hz if the physiological pulses originate from the breathing system, approx. 0.04-0.14 Hz if the physiological pulses originate from the autonomous systems for blood pressure regulation, and approx. 0.001-0.1 Hz if the physiological pulses originate from autonomous system for temperature regulation.

Figure 10:
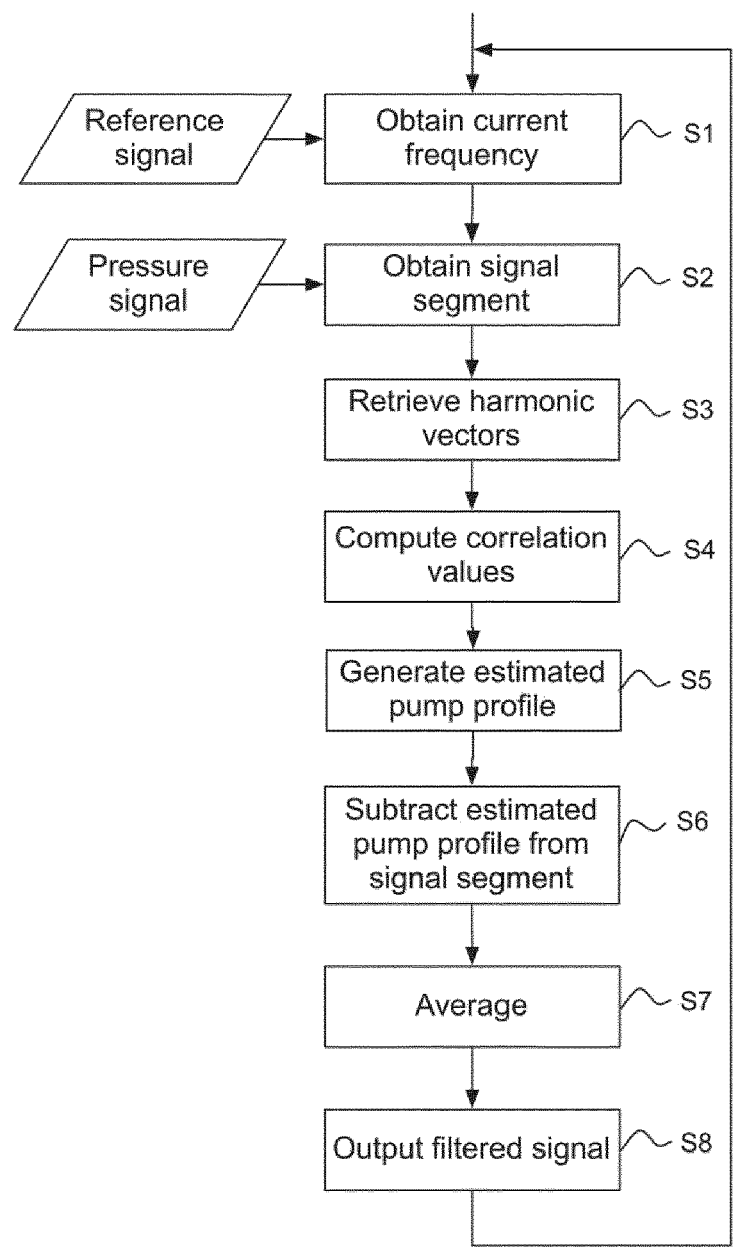
FIG. 10 is a flow chart of an embodiment of a method of filtering a pressure signal.

FIG. 10 shows a detailed example of a filtering process performed by the device 7 in FIG. 4. The method operates in a repeating sequence of steps S1-S8. In step S1, a current frequency of the pump 4 is identified based on the reference signal. In step S2, a signal segment is obtained from a time window in the pressure signal to form the pressure vector $\bar{p}$ such that its pressure values are in temporal alignment with the signal values in a set of predefined harmonic vectors $\bar{v}_k$. In step S3, the set of predefined harmonic vectors $\bar{v}_k$ are retrieved from electronic memory 9b. The set of predefined harmonic vectors $\bar{v}_k$ include a sine wave and a cosine wave at each of a plurality of predefined nominal harmonic frequencies. By the temporal alignment of the pressure vector $\bar{p}$ according to step S2, the set of predefined harmonic vectors $\bar{v}_k$ are effectively adapted to the current frequency of the pump 4. As noted above, step S3 may instead involve the harmonic vectors $\bar{v}_k$ being generated by the processor 9a. In step S4, the correlation values $\hat{\lambda}_k$ are computed between the pressure vector $\bar{p}$ and each of the predefined harmonic vectors $\bar{v}_k$, according to Eq. (2). In step S5, the harmonic vectors $\bar{v}_k$ are linearly combined by the correlation values $\hat{\lambda}_k$ to form the estimated pump profile $\hat{d}$, according to Eq. (4). In step S6, the estimated pump profile $\hat{d}$ is subtracted from the pressure vector $\bar{p}$ to form the filtered signal vector $\bar{e}$, according to Eq. (3). In step S7, if the consecutive time windows overlap, filtered signal values are formed by temporally aligning and combining (e.g. by averaging) overlapping portions of consecutive vectors $\bar{e}$. In step S8, the filtered signal values are output as a filtered signal e.

Figure 11:
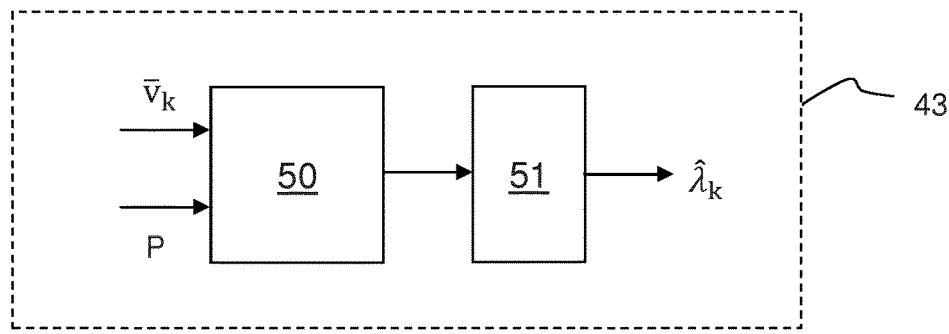
FIG. 11 is a block diagram of an embodiment of a correlation block in FIG. 4.

There are alternative ways of generating the correlation values $\hat{\lambda}_k$. In one embodiment, schematically indicated in FIG. 11, the correlator 43 operates on individual values instead of vectors. The correlator 43 comprises multiplier blocks 50 (one shown) that multiplies incoming pressure values in the pressure signal (from the input block 41) by individual signal values in a respective harmonic signal $\bar{v}_k$ (at a harmonic frequency identified by harmonics detector 42) to generate a respective product signal that forms a time sequence of product values. A low-pass filter 51 is applied to the respective product signal to generate a respective time sequence of (estimated) correlation values for the respective harmonic signal $\bar{v}_k$. Any known type of low-pass filter 51 may be used, as well as any combination of such low-pass filters. Generally, the low-pass filter 51 results in an aggregation of the respective time sequence of product values within a time window in the pressure signal. In one presently preferred embodiment, the filter 51 is a moving average filter with a length equal a multiple of the period of the smallest harmonic frequency. Thereby, the output values of the filter 51 are equivalent to the correlation values produced by the correlator 43 in FIG. 4 for the pressure vectors $\bar{p}$. Irrespective of the type of filter 51, the correlator 43 in FIG. 11 may be configured to supply a set of correlation values $\hat{\lambda}_k$ for a time window in the pressure signal P, and these correlation values $\hat{\lambda}_k$ may then be used by the subtraction block 44 in the same way as described in relation to FIG. 4. Thus, the subtraction block 44 may be designed to subtract, from a pressure vector $\bar{p}$ obtained from the pressure signal P, a linear combination of harmonic vectors (at the harmonic frequencies identified by harmonic detector 42) using the correlation vectors $\hat{\lambda}_k$ as coefficients. In a variant, the subtraction block 44 may be designed to subtract the harmonic signals used by the multiplier blocks 50 from the pressure signal P, using the correlation vectors $\hat{\lambda}_k$ as coefficients.

Irrespective of representation, the filtering device 7 may be implemented by special-purpose software (or firmware) run on one or more general-purpose or special-purpose computing devices. In this context, it is to be understood that an "element" or "means" of such a computing device refers to a conceptual equivalent of a method step; there is not always a one-to-one correspondence between elements/means and particular pieces of hardware or software routines. One piece of hardware sometimes comprises different means/elements. For example, a processing unit serves as one element/means when executing one instruction, but serves as another element/means when executing another instruction. In addition, one element/means may be implemented by one instruction in some cases, but by a plurality of instructions in some other cases. Such a software controlled computing device may include one or more processing units (cf. 9a in FIG. 1), e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The device 7 may further include a system memory and a system bus that couples various system components including the system memory (cf. 9b in FIG. 1) to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The device 7 may include one or more communication interfaces, such as a serial interface, a parallel interface, a USB interface, a wireless interface, a network adapter, etc, as well as one or more data acquisition devices, such as an A/D converter. The special-purpose software may be provided to the device 7 on any suitable computer-readable medium, including a record medium or a read-only memory.

It is also conceivable that some (or all) elements/means are fully or partially implemented by dedicated hardware, such as an FPGA, an ASIC, or an assembly of discrete electronic components (resistors, capacitors, operational amplifier, transistors, filters, etc), as is well-known in the art.

It should be emphasized that the invention is not limited to digital signal processing, but could be fully implemented by a combination of analog devices.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

For example, as an alternative to calculating all correlation values $\hat{\lambda}_k$ with respect to the same time window in the pressure signal P, e.g. as illustrated in FIGS. 6-7, the correlation value $\hat{\lambda}_k$ for a respective harmonic frequency may be calculated by correlation with pressure values in a time window that matches a given multiple of the respective harmonic frequency. Thereby, different numbers of correlation values $\hat{\lambda}_k$ are obtained at different harmonic frequencies for a given segment in pressure signal P. The skilled person realizes that the harmonics may be combined into an estimated pump profile using the resulting set of correlation values $\hat{\lambda}_k$.

Furthermore, as an alternative to subtracting all harmonics when all correlation values $\hat{\lambda}_k$ have been determined for a time window, it is conceivable to subtract the harmonics sequentially. In one such implementation, the pressure vector $\bar{p}$ is updated between each correlation with the respective harmonic(s) at a given harmonic frequency, such that the respective harmonic(s) are subtracted from the pressure vector $\bar{p}$ using the resulting correlation value(s) $\hat{\lambda}_k$. Thereby, the content of the pressure vector $\bar{p}$ changes between every correlation, until it contains the filtered signal vector $\bar{e}$ after the last update.

It is also to be understood that the correlation values $\hat{\lambda}_k$ may be estimated by other functions than the above-described dot product which results in a non-weighted summation of product values. For example, it is conceivable to use a weighted summation.

The skilled person realizes that all examples given with reference to the drawings presume that the reference signal REF is a different signal than the pressure signal P. However, as noted, it is possible to use the pressure signal P itself as reference signal. If the pressure signal P is used as reference signal, step S1 in FIG. 10 is modified such that the current frequency of the pump is identified based on the pressure signal P. Further, even if it is possible to provide the pressure signal P to both input blocks 40, 41 in FIG. 4, it is also conceivable that the input block 40 is omitted and that the device 7 is designed to supply the pressure signal P from the input block 41 to the harmonics detector 42 in addition to the correlator 43 and the subtraction block 44. Thus, the harmonics detector 42 is configured to process the pressure signal P to identify the current harmonic frequencies generated by the pump.

Further, the pressure sensor may be of any type, e.g. operating by resistive, capacitive, inductive, magnetic, acoustic or optical sensing, and using one or more diaphragms, bellows, Bourdon tubes, piezo-electrical components, semiconductor components, strain gauges, resonant wires, accelerometers, etc. For example, the pressure sensor may be implemented as a conventional pressure sensor, a bioimpedance sensor, a photoplethysmography (PPG) sensor, etc.

The inventive filtering technique is applicable for processing a pressure signal obtained from a pressure sensor in all types of fluid containing systems, especially in systems for medical or therapeutic use, to suppress or essentially remove periodic interferences ("first pulses") originating from a periodic pulse generator, which is located in or is associated with the fluid containing system. In this context, "associated with" implies that the periodic pulse generator need not be included in the fluid containing system but is capable of generating pressure waves that propagate in the fluid containing system to the pressure sensor. The resulting filtered signal contains pressure variations ("second pulses"), which may be periodic or not. The inventive filtering technique allows the filtered signal to be processed for analysis of the pressure variations, for any purpose, irrespective of the periodic disturbances in the pressure signal.

For example, the inventive filtering technique is applicable in all types of EC circuits in which blood is taken from the systemic blood circuit of the patient to have a process applied to it before it is returned to the patient. Such EC circuits include circuits for hemodialysis, hemofiltration, hemodiafiltration, plasmapheresis, apheresis, extracorporeal membrane oxygenation, assisted blood circulation, and extracorporeal liver support/dialysis. The inventive technique is likewise applicable for filtering in other types of EC circuits, such as circuits for blood transfusion, as well as heart-lung-machines.

The inventive technique is also applicable to fluid systems that contain other liquids than blood and are connected to the cardiovascular system of a human or animal subject, including systems for intravenous therapy, infusion pumps, automated peritoneal dialysis (APD) systems, etc. Examples of such liquids include medical solutions, dialysis fluids, infusion liquids, water, etc.

It should be emphasized that the fluid containing system need not be connected to a human or animal subject. For example, the fluid containing system may be a regeneration system for dialysis fluid, which circulates dialysis fluid from a supply through a regeneration device and back to the supply. In another example, the fluid containing system is an arrangement for priming an EC circuit by pumping a priming fluid from a supply via the EC circuit to a dialyser. In a further example, the fluid containing system is an arrangement for purifying water, which pumps water from a supply through a purifying device.

The inventive technique is applicable for removing or suppressing pressure pulses that originate from any type of periodic pulse generator, be it mechanic or human, which is arranged in or associated with the fluid containing system. The periodic pulse generator may be any type of pumping device, not only rotary peristaltic pumps as disclosed above, but also other types of positive displacement pumps, such as linear peristaltic pumps, diaphragm pumps, as well as centrifugal pumps. Further, the periodic pulse generator may be one or more valves or flow restrictors that are installed in or associated with the fluid containing system. The valves and flow restrictors may be operable to periodically stop a flow of fluid, change a flow rate of fluid, or change a fluid flow path. The valves and flow restrictors may also be included in a system for degassing of a fluid or a system for changing the static pressure of a fluid. In another example, the periodic pulse generator is a balancing chamber as used in certain types of dialysis systems.

Likewise, the inventive technique is applicable to produce a filtered signal with pressure variations or pressure pulses ("second pulses") originating from any type of pulse generator, be it human or mechanic.

The inventive technique need not operate on real-time data, but could be used for processing off-line data, such as a previously recorded pressure signal.

The invention claimed is:

1. A device for filtering a pressure signal obtained from a pressure sensor in a fluid containing system, the pressure signal comprising first pulses and second pulses, the first pulses originating from a first periodic pulse generator, said device comprising:
   an input for receiving the pressure signal from the pressure sensor; and
   a signal processor connected to the input, the signal processor configured to:
      determine, based on a reference signal, a plurality of harmonic frequencies associated with the first pulses, wherein the reference signal is indicative of a current operating frequency of the first periodic pulse generator;
      determine, for a time window within the pressure signal, a pressure vector of pressure values within the time window;
      determine, for the time window within the pressure signal, a first harmonic vector and a second harmonic vector for each of the plurality of harmonic frequencies, wherein each first harmonic vector defines a sine wave at a respective harmonic frequency of the plurality of harmonic frequencies, and wherein each second harmonic vector defines a cosine wave at the respective harmonic frequency;
      compute, for the time window within the pressure signal, correlation values between (i) each first harmonic vector and the pressure vector and (ii) each second harmonic vector and the pressure vector; and generate a filtered signal including the second pulses and removing the first pulses by (i) combining, as a function of the correlation values, each of the first and second harmonic vectors and (ii) subtracting the combined first and second harmonic vectors from the pressure vector.

2. The device of claim 1, wherein the signal processor is configured to, when computing the correlation value between a respective first or second harmonic vector and the pressure vector, generate product values by multiplying individual pressure values in the pressure vector by individual values in the respective first or second harmonic vector, and generate the correlation value as a function of a time-sequence of the product values.

3. The device of claim 2, wherein the signal processor is configured to select the time-sequence of product values to correspond to at least one period of the respective harmonic frequency.

4. The device of claim 2, wherein the signal processor is configured to select the time-sequence of product values to match a whole number of periods of the respective harmonic frequency.

5. The device of claim 2, wherein the signal processor is configured to generate the correlation value as a summation, weighted or non-weighted, of the time-sequence of product values.

6. The device of claim 2, wherein the signal processor is configured to operate a low-pass filter on the time-sequence of product values, and obtain the correlation value of the respective first or second harmonic vector based on an output signal of the low-pass filter.

7. The device of claim 1, wherein the signal processor is configured to, when computing the correlation values, set each of the first and second harmonic vectors to have a correlation time window that matches the time window.

8. The device of claim 1, wherein the signal processor is configured to compute a scalar product between the pressure vector and each of the first and second harmonic vectors, and obtain the correlation values based on the computed scaler products.

9. The device of claim 8, wherein the signal processor is configured to generate the correlation values based on the same pressure vector.

10. The device of claim 1, wherein each of the first and second harmonic vectors is set to have a fixed value within the time window.

11. The device of claim 1, wherein the signal processor is further configured to, before computing the correlation values, process the pressure signal for selective removal of frequencies outside a predefined frequency range associated with the second pulses, and wherein the signal processor is configured to limit the plurality of harmonic frequencies to the predefined frequency range.

12. The device of claim 1, wherein the signal processor is configured to generate the filtered signal by combining each of the first and second harmonic vectors as a function of the correlation values to form a predicted temporal signal profile of the first pulses within the time window, and subtract the predicted temporal profile from the pressure vector.

13. The device of claim 1, wherein the signal processor is configured to generate the filtered signal by subtracting a linear combination of each of the first and second harmonic vectors using the correlation values as coefficients.

14. The device of claim 1, wherein the signal processor is configured to repeatedly generate the filtered signal for a sequence of time windows to at least substantially eliminate the first pulses while retaining the second pulses.

15. The device of claim 14, wherein the time windows in the sequence of time windows are non-overlapping.

16. The device of claim 14, wherein the time windows in the sequence of time windows are partially overlapping, wherein each subtraction of the first and second harmonic vectors from the pressure vector within the time window of the pressure signal results in a filtered signal segment, said signal processor being further configured to generate the filtered signal by combining overlapping signal values in the filtered signal segments.

17. The device of claim 1, wherein the fluid containing system comprises an extracorporeal blood flow circuit connected to a blood system in a human body, and wherein the first periodic pulse generator comprises a pumping device in the extracorporeal blood flow circuit, and wherein the second pulses originate from a physiological pulse generator in the human body.

18. The device of claim 1, wherein each correlation value estimates an amplitude and a phase of a respective harmonic frequency of the plurality of harmonic frequencies.

19. A fluid containing system operable to filter a pressure signal, the pressure signal comprising first pulses and second pulses, the first pulses originating from a first periodic pulse generator, said system comprising:
 a pressure sensor configured to generate the pressure signal; and
 a signal processor configured to:
  receive the pressure signal from the pressure sensor;
  determine, based on a reference signal, a plurality of harmonic frequencies associated with the first pulses, wherein the reference signal is indicative of a current operating frequency of the first periodic pulse generator;
  determine, for a time window within the pressure signal, a pressure vector of pressure values within the time window;
  determine, for the time window within the pressure signal, a first harmonic vector and a second harmonic vector for each of the plurality of harmonic frequencies, wherein each first harmonic vector defines a sine wave at a respective harmonic frequency of the plurality of harmonic frequencies, and wherein each second harmonic vector defines a cosine wave at the respective harmonic frequency;
  compute, for the time window within the pressure signal, correlation values between (i) each first harmonic vector and the pressure vector and (ii) each second harmonic vector and the pressure vector; and
  generate a filtered signal including the second pulses and removing the first pulses by (i) combining, as a function of the correlation values, each of the first and second harmonic vectors and (ii) subtracting the combined first and second harmonic vectors from the pressure vector.

20. A method of filtering a pressure signal obtained from a pressure sensor in a fluid containing system, the pressure signal comprising first pulses and second pulses, the first pulses originating from a first periodic pulse generator, said method comprising the steps of:
 obtaining the pressure signal from the pressure sensor;
 determining, based on a reference signal, a plurality of harmonic frequencies associated with the first pulses, wherein the reference signal is indicative of a current operating frequency of the first periodic pulse generator;

determining, for a time window within the pressure signal, a pressure vector of pressure values within the time window;

determining, for the time window within the pressure signal, a first harmonic vector and a second harmonic vector for each of the plurality of harmonic frequencies, wherein each first harmonic vector defines a sine wave at a respective harmonic frequency of the plurality of harmonic frequencies, and wherein each second harmonic vector defines a cosine wave at the respective harmonic frequency;

computing, for the time window within the pressure signal, correlation values between (i) each first harmonic vector and the pressure vector and (ii) each second harmonic vector and the pressure vector; and generating a filtered signal including the second pulses and removing the first pulses by (i) combining, as a function of the correlation values, each of the first and second harmonic vectors and (ii) subtracting the combined first and second harmonic vectors from the pressure vector.

21. A non-transitory computer-readable medium for filtering a pressure signal obtained from a pressure sensor in a fluid containing system, the pressure signal comprising first pulses and second pulses, the first pulses originating from a first periodic pulse generator, the non-transitory computer-readable medium comprising:

computer instructions which, when executed by a processor, cause the processor to:

obtain a pressure signal from the pressure sensor;

determine, based on a reference signal, a plurality of harmonic frequencies associated with the first pulses, wherein the reference signal is indicative of a current operating frequency of the first periodic pulse generator;

determine, for a time window within the pressure signal, a pressure vector of pressure values within the time window;

determine, for the time window within the pressure signal, a first harmonic vector and a second harmonic vector for each of the plurality of harmonic frequencies, wherein each first harmonic vector defines a sine wave at a respective harmonic frequency of the plurality of harmonic frequencies, and wherein each second harmonic vector defines a cosine wave at the respective harmonic frequency;

compute, for the time window within the pressure signal, correlation values between (i) each first harmonic vector and the pressure vector and (ii) each second harmonic vector and the pressure vector; and generate a filtered signal including the second pulses and removing the first pulses by (i) combining, as a function of the correlation values, each of the first and second harmonic vectors and (ii) subtracting the combined first and second harmonic vectors from the pressure vector.

* * * * *